United States Patent

Disch et al.

[11] Patent Number: 5,824,708
[45] Date of Patent: Oct. 20, 1998

[54] VIRUCIDAL SUBSTANCES

[75] Inventors: Karl-Heinz Disch, Haan; Klaus-Peter Bansemir, Langenfeld; Klaus Hachmann, Hilden; Friedrich von Rheinbaben, Duesseldorf, all of Germany

[73] Assignee: Henkel - Ecolab GmbH & Co. OHG, Duesseldorf, Germany

[21] Appl. No.: 649,714

[22] PCT Filed: Nov. 17, 1994

[86] PCT No.: PCT/EP94/03812

§ 371 Date: Jun. 27, 1996

§ 102(e) Date: Jun. 27, 1996

[87] PCT Pub. No.: WO95/14382

PCT Pub. Date: Jun. 1, 1995

[30] Foreign Application Priority Data

Nov. 25, 1993 [DE] Germany .......................... 43 40 124.4

[51] Int. Cl.$^6$ .......................... A01N 37/12; C07C 229/00
[52] U.S. Cl. .......................... 514/563; 514/564; 514/561; 562/561; 562/564
[58] Field of Search ..................... 514/561, 563, 514/564; 562/561, 564

[56] References Cited

U.S. PATENT DOCUMENTS 4,652,585  3/1987  Gerhardt et al. .......................... 514/563

FOREIGN PATENT DOCUMENTS 156 275    10/1985   European Pat. Off. .
34 10 956   9/1985   Germany .
94 25559   11/1994   WIPO .

OTHER PUBLICATIONS

Bundesgensundheitsamt: Guidelines of the Bundesgesundeitsamt (BGA; German Federal Health Office) and the Deutsche Vereinigung zur Bekämpfung der Viruskrankheiten e.V. 9DVV: German Association for the Control of Virus Diseases) for Testing the Effectiveness of Chemical Disinfectants Against Viruses. Zbl. Hyg. 1990; 189: 554–62).

*Primary Examiner*—Michael P. Woodward
*Attorney, Agent, or Firm*—Ernest G. Szoke; Wayne C. Jaeschke; Real J. Grandmaison

[57] ABSTRACT

The process of reducing the count of a virus by contacting the virus with
  (1) the reaction product of
    a) N-substituted propylenediamines corresponding to formula I:

$$R^1-NH-CH_2-CH_2-CH_2-NH_2 \qquad (I)$$

In which $R^1$ is a linear alkyl radical containing 12 to 14 carbon atoms, with
    b) compounds corresponding to formula II:

$$R^2-O-CO-CH_2-CH_2-\underset{\underset{NH_2}{|}}{CH}-COOH \qquad (II)$$

in which $R^2$ is an alkyl radical containing 1 to 4 carbon atoms or a hydrogen atom, the molar ratio of a) to b) is 1:1 to 1:2 and the reaction is carried out over a period of 0.5 to 10 hours at 60° C. to 175° C. with elimination of alcohol or water, and optionally,
  (2) wherein the reaction product is further reacted with ethylene oxide or propylene oxide, and optionally,
  (3) salt formation of the products obtained in (1) or (2) with inorganic or organic acids.

2 Claims, No Drawings

VIRUCIDAL SUBSTANCES

BACKGROUND OF THE INVENTION

1. Field of the Invention

DE 34 10 956 A1 relates to antimicrobial agents obtainable by 1) reaction of
   a) N-substituted propylenediamines corresponding to formula I:

$$R^1\text{—NH—CH}_2\text{—CH}_2\text{—CH}_2\text{—NH}_2 \quad (I)$$

In which $R^1$ is a linear alkyl radical containing 12 to 14 carbon atoms, with
   b) compounds corresponding to formula II:

$$R^2\text{—O—CO—CH}_2\text{—CH}_2\text{—CH(NH}_2)\text{—COOH} \quad (II)$$

in which $R^2$ is an alkyl radical containing 1 to 4 carbon atoms or a hydrogen atom, the molar ratio of a) to b) being 1:1 to 1:2 and the reaction being carried out over a period of 0.5 to 10 hours at 60° to 175° C. with elimination of alcohol and/or water, and optionally 2) further reaction of the products obtained in 1) with ethylene oxide or propylene oxide under alkoxylation conditions known per se and optionally 3) salt formation of the products obtained in 1) or 2) with inorganic or organic acids.

By virtue of their microbistatic and microbicidal effect on bacteria and fungi, these antimicrobial agents are suitable for solving various disinfection or preservation problems in non-therapeutic applications. For use as an active ingredient in antimicrobial formulations, they may be incorporated in liquid, paste-form or solid preparations. The corresponding preparations are used for various purposes, for example as cleaners, disinfectants and preservatives for textiles, floors, hospital equipment, medical instruments, schools, swimming pools, public transport, commercial enterprises, such as dairies, breweries and laundries.

2. Description of the Invention

The present invention relates to the use of the active substances defined above as virucidal agents.

In principle, bactericidal or fungicidal agents cannot be expected to show virucidal activity as well, Basically, bactericides, for example any of the usual so-called active ingredients of disinfectants, are not virucidal as well. In many cases, however, they are partly virucidal against lipophilic enveloped viruses, for example against Newcastle Disease virus, herpes viruses or vaccinia virus.

A partly virucidal spectrum such as this is a known attribute of a number of surfactants, quaternary ammonium compounds and biguanides. However, these substances are either ineffectual or show inadequate activity against lipophilic, envelope-free viruses, for example adenovirus or SV 40 tumor virus.

The highest degree of virucidal activity is only achieved by very few substances, for example by aldehydes, more especially formaldehyde, glutaralde-hyde, or certain oxygen- or halogen-yielding substances. The substances in question would even destroy the hydrophilic envelope-free viruses which are the most difficult to inactivate, such as polio virus for example.

In tests, the known active substance according to DE 34 10 956 A1 showed hitherto unknown and unforeseeable effectiveness both against enveloped lipophilic viruses and against envelope-free lipophilic viruses (cf. Tables 1 and 2). Accordingly, the active substance according to DE 34 10 956 A1 which is known to be antimicrobial is also a new virucidal agent. Under comparable conditions, it shows considerably better virucidal activity than Vantocil® (a polymeric biguanide produced by ICI), cf. Table 3. This applies both to solutions in butyl diglycol and to solutions in water.

EXPERIMENTAL DATA

The virucidal performance of the active substance according to DE 34 10 956 A1 and of Vantocil® was tested against the following viruses by the DVV method (Bundesgesundheitsamt: Guidelines of the Bundesgesundheitsamt (BGA; German Federal Health Office) and the Deutsche Vereinigung zur Bekämpfung der Viruskrankheiten e.V. (DW: German Association for the Control of Virus Diseases) for Testing the Effectiveness of Chemical Disinfectants Against Viruses. Zbl. Hyg. 1990; 189: 554–62):

Newcastle Disease virus (NDV) lipophilic enveloped virus

Herpes Simplex virus (HSV) lipophilic enveloped virus

Vaccinia virus (Vacc) lipophilic enveloped virus

Adenovirus (Adeno) lipophilic envelope-free virus

SV40 Tumor virus (SV40) lipophilic envelope-free virus

The results of the tests involving the substances mentioned in in-use concentrations of 0.005 to 1% are set out in Tables 1 to 3 for the viruses mentioned above. The figures shown represent the reduction factors (log 10) in respect of the particular viruses for contact times of 15, 30 and 60 minutes. The abbreviations used in the Tables have the following meanings:

IUC=in-use concentration

CT=contact time

NPC=no protein challenge

FCS=10% foetal calf serum as protein challenge

BSA=0.2% bovine serum albumin as protein challenge cbe.=cannot be evaluated

AS:=active substance

TABLE 1

Virucidal activity of the active substance according to DE 34 10 956 A1 (50% variant with butyl diglycol as solvent). Titer reduction (log 10) of the particular viruses listed under the conditions mentioned (contact times and in-use concentrations).

| Product | IUC(AS) In % | Virus | CT in Minutes 15 | 30 | 60 |
|---|---|---|---|---|---|
| Active substance according to DE 34 10 956 | 0.005 | NDV | 2 | 2 | 2.3 |
| | 0.01 | | 1.5 | 2.2 | 2.3 |
| | 0.05 | | 2.3 | 2.4 | 2.2 |
| | 0.1 | | >4.5 | >4,5 | >4,5 |
| | 0.5 | | >4.5 | >4.5 | >4.5 |
| | 1.0 | | >3.5 | >3.5 | >3.5 |
| Active substance according to DE 34 10 956 | 0.005 | HSV | 1 | 1.5 | 2 |
| | 0.01 | | 4.2 | >5 | >5 |
| | 0.05 | | >5 | >5 | >5 |
| | 0.1 | | >4 | >4 | >4 |
| | 0.5 | | >4 | >4 | >4 |
| | 1.0 | | >3 | >3 | >3 |
| Active substance according to DE 34 10 956 | 0.005 | Vacc. | 2.5 | 2.5 | 2.9 |
| | 0.01 | | 2.9 | 2.9 | 3 |
| | 0.05 | | >3.5 | >3.5 | >3.5 |

TABLE 1-continued

Virucidal activity of the active substance according to DE 34 10 956 A1 (50% variant with butyl diglycol as solvent). Titer reduction (log 10) of the particular viruses listed under the conditions mentioned (contact times and in-use concentrations).

| Product | IUC(AS) In % | Virus | CT in Minutes 15 | 30 | 60 |
|---|---|---|---|---|---|
|  | 0.1 |  | >3.5 | >3.5 | >3.5 |
|  | 0.5 |  | >2.5 | >2.5 | >2.5 |
|  | 1.0 |  | >2.5 | >2.5 | >2.5 |
| Active substance according to DE 34 10 956 | 0.005 | Adeno | 0 | 0.2 | 2 |
|  | 0.01 |  | 1.4 | 1.2 | 2 |
|  | 0.05 |  | 3.5 | >4.5 | >4.5 |
|  | 0.1 |  | 3.4 | >3.5 | >3.5 |
|  | 0.5 |  | >3.5 | >3.5 | >3.5 |
|  | 1.0 |  | >2.5 | >2.5 | >2.5 |
| Active substance according to DE 34 10 956 | 0.005 | SV40 | 2 | 2 | 2 |
|  | 0.01 |  | 2.3 | 1.8 | 2.3 |
|  | 0.05 |  | 3.3 | >4.5 | 3.9 |
|  | 0.1 |  | >3.5 | >3.5 | >3.5 |
|  | 0.5 |  | >3.5 | >3.5 | >3.5 |
|  | 1.0 |  | >3.5 | >3.5 | >3.5 |

TABLE 2

Viruddal activity of the active substance according to DE 34 10 956 A1 (33.3% variant with water as solvent). Titer reduction (log 10) of the particular viruses listed under the conditions mentioned (contact times and in use concentrations).

| Product | IUC(AS) In % | Virus | CT in Minutes 15 | 30 | 60 |
|---|---|---|---|---|---|
| Active substance according to DE 34 10 956 | 0.005 | NDV | 1.5 | 2 | 2.2 |
|  | 0.01 |  | 2 | 2.2 | 2 |
|  | 0.05 |  | 1.5 | 2.4 | 1.7 |
|  | 0.1 |  | >4.5 | >4.5 | >4.5 |
|  | 0.5 |  | >4.5 | >4.5 | >4.5 |
|  | 1.0 |  | >3.5 | >3.5 | >3.5 |
| Active substance according to DE 34 10 956 | 0.005 | HSV | 1.5 | 1.5 | 2.5 |
|  | 0.01 |  | 3.9 | 4.5 | >5 |
|  | 0.05 |  | >5 | >5 | >5 |
|  | 0.1 |  | >4 | >4 | >4 |
|  | 0.5 |  | >3 | >3 | >3 |
|  | 1.0 |  | >3 | >3 | >3 |
| Active substance according to DE 34 10 956 | 0.005 | Vacc. | 2.8 | 3 | 3 |
|  | 0.01 |  | 2.9 | 3 | 3 |
|  | 0.05 |  | >3.5 | >3.5 | >3.5 |
|  | 0.1 |  | >3.5 | >3.5 | >3.5 |
|  | 0.5 |  | >2.5 | >2.5 | >2.5 |
|  | 1.0 |  | >2.5 | >2.5 | >2.5 |
| Active substance according to DE 34 10 956 | 0.005 | Adeno | 0.5 | 1 | 1.8 |
|  | 0.01 |  | 1.2 | 1 | 2 |
|  | 0.05 |  | 1.5 | >3.5 | >3.5 |
|  | 0.1 |  | 1.9 | >3.5 | >3.5 |
|  | 0.5 |  | 2 | 2.5 | >3.5 |
|  | 1.0 |  | 2 | 2.3 | >2.5 |
| Active substance according to DE 34 10 956 | 0.005 | SV40 | 1.8 | 2 | 1.8 |
|  | 0.01 |  | 1.9 | 2 | 2 |
|  | 0.05 |  | >3.5 | >3.5 | >3.5 |
|  | 0.1 |  | >3.5 | >3.5 | >3.5 |
|  | 0.5 |  | >3.5 | >3.5 | >3.5 |
|  | 1.0 |  | >3.5 | >3.5 | >3.5 |

TABLE 3

Virucidal activity of Vantocil ® (20% raw material). Titer reduction (log 10) of the particular viruses listed under the conditions mentioned (contact times and in-use concentration).

| Product | IUC(AS) In % | Virus | CT in Minutes 15 | 30 | 60 |
|---|---|---|---|---|---|
| Vantocil | 0.005 | HSV | 0 | 0 | 0 |
|  | 0.01 |  | 0 | 0 | 0 |
|  | 0.05 |  | 0.5 | 1.3 | 1.8 |
|  | 0.1 |  | 1.3 | 2 | 2.5 |
|  | 0.5 |  | 1.9 | 2.9 | >3.5 |
|  | 1.0 |  | 3.2 | >3.5 | >3.5 |
| Vantocil | 0.005 | Vacc. | 0.5 | 0.7 | 0.9 |
|  | 0.01 |  | 1.3 | 1.5 | 1.5 |
|  | 0.05 |  | 1.9 | 1.9 | 2.3 |
|  | 0.1 |  | 1.9 | 1.9 | 2.3 |
|  | 0.5 |  | 1 | 1 | 1.2 |
|  | 1.0 |  | 0.4 | 1.3 | 1.9 |
| Vantocil | 0.005 | Adeno | 0.5 | 0.5 | 0.5 |
|  | 0.01 |  | 0.5 | 0.7 | 0.8 |
|  | 0.05 |  | 1 | 1.7 | 1.9 |
|  | 0.1 |  | 1.2 | 1.8 | 1.9 |
|  | 0.5 |  | 1.7 | 1.8 | 1.9 |
|  | 1.0 |  | 1.7 | 1.5 | 1.5 |
| Vantocil | 0.005 | SV40 | 1 | 1.3 | 1.5 |
|  | 0.01 |  | 1.3 | 1.5 | 1.8 |
|  | 0.05 |  | cbe. | 1 | 1.5 |
|  | 0.1 |  | 1.4 | 1.5 | 2 |
|  | 0.5 |  | 1 | 1.8 | 1.7 |
|  | 1.0 |  | 1.3 | 2 | 2 |

In addition to the described active ingredient, the final virucidal formulations may generally contain other ingredients typically used in such formulations which are selected according to the form of application and purpose envisaged. Solvents for liquid formulations include water and typical water-soluble and sparingly water-soluble organic solvents, optionally in admixture with water. Preferred organic solvents are those from the groups of aliphatic and aromatic alcohols containing 1 to 5 carbon atoms in the alkyl chains, glycols containing 2 to 4 carbon atoms and the diglycols and diglycol ethers derivable therefrom. Examples of corresponding solvents are methanol, ethanol, propanol, isopropanol, tert.butanol, ethylene glycol, propylene glycol, butylene glycol, diethylene glycol, dipropylene glycol, diethylene glycol monomethyl ether, diethylene glycol monoethyl ether, diethylene glycol monopropyl ether and diethylene glycol monobutyl ether, more especially butyl diglycol but also triethyl acetate and triethyl citrate. If it is desired to obtain clear, cleaning virucidal formulations, aromatic alcohols, such as benzyl alcohol and/or 2-phenoxyethanol and/or 1-phenoxypropanol, are best added in addition to the other solvents. A mixture of benzyl alcohol and 1-phenoxypropanol, above all in a quantity ratio of about 1:1, is preferred. By using these alcohols as solubilizers, the clear point of the virucidal formulations in typical solvents could be reduced to temperatures well below 20° C. They remained stable in storage over an observation period of around 9 months. They may be used in quantities of around 3 to 40% by weight and preferably in quantities of around 10 to 20% by weight.

If a cleaning effect is required in addition to the virucidal effect, the formulations may contain nonionic, anionic or amphoteric surfactants. Suitable nonionic surfactants are, for example, alkyl polyglycosides preferably containing 8 to 22 carbon atoms in the alkyl chain, reaction products of 4 to 40 and preferably 4 to 20 mole equivalents of ethylene oxide (EO) and/or propylene oxide (PO) with fatty alcohols, fatty acids, fatty amines, fatty acid amides or alkanesulfonamides, of which the fatty alkyl radicals each preferably contain 8 to 22 carbon atoms, and with alkylphenols and also amine oxides. The end-capped derivatives of such alkoxylation products, preferably containing terminal groups with 2 to 10 carbon atoms, are also suitable. Adducts of 5 to 16 moles of ethylene oxide with cocofatty alcohols or tallow fatty alcohols, with oleyl alcohol and with mono-, di- or trialkylphenols and with monoalkyl cyclohexanols containing 6 to 14 carbon atoms in the alkyl chains are of particular interest. It can be of advantage to use the lowest-foaming representatives of this group. Corresponding nonionic surfactants include, for example, the commercial products Dehypon® LS 24, LS 36, LS 45, LS 54, LT 24, LT 104 and LS 104, OCP 502 (Henkel KGaA), Dehydol® LT 30 (Henkel KGaA), Lutensol® LF 224, LT 30 (BASF), Triton® CF 54 and DF 12 (Röhm & Haas). The nonionic surfactants are used in quantities of about 3 to 20% by weight and preferably in quantities of about 5 to 10% by weight.

Suitable amphoteric surfactants are derivatives of tertiary aliphatic amines or quaternary aliphatic ammonium compounds of which the aliphatic radicals may be linear or branched and of which one bears a carboxy, sulfo, phosphono, sulfato or phosphato group. Examples of such amphoteric surfactants are dimethyl tetradecyl glycine, dimethyl hexadecyl glycine, dimethyl octadecyl glycine, 3-(dimethyidodecylammonio)-1-propane sulfonate and the amphoteric surfactants marketed by Henkel KGaA under the names of Dehyton®, AB, CB and G. They are used in quantities of about 0 to 10% by weight and preferably in quantities of about 2 to 5% by weight.

In order to obtain a clear in-use solution and to guarantee favorable anticorrosion behavior where the cleaning concentrates according to the invention are used with hard water, the cleaners and disinfectants according to the invention may contain complexing agents or corrosion inhibitors, preferably selected from the groups of phosphonic acids, aminocarboxylic acids and salts thereof, more especially their alkali metal salts. Examples of these complexing agents are the alkali metal salts, preferably the sodium salts, of methane diphosphonic acid, hydroxyethane-1,1-diphosphonic acid, 1-aminoethane-1,1-diphosphonic acid, amino-tri-(methylenephosphonic acid), ethylenediamine tetra-(methylenephosphonic acid), diethylenetriamine penta-(methylenephosphonic acid), 2-phosphonobutane-1,2, 4-tricarboxylic acid, nitrilotriacetic acid (NTA), ethylenediamine tetraacetic acid and hydroxyethyl ethylenediamine triacetic acid. NTA is preferred. 1,2,3-Benzotriazole may also be used as a pure corrosion inhibitor. Corresponding complexing agents and corrosion inhibitors are preferably present in the formulations according to the invention in quantities of not more than 6% by weight and more especially in quantities of about 0.5% by weight to 3% by weight.

The cleaning and disinfecting concentrates according to the invention may also contain additives of the type typically encountered in such formulations, such as dyes or fragrances. These typical additives are preferably present in the formulations according to the invention in quantities of not more than 1% by weight.

The active substance according to DE 34 10 956 used in accordance with the invention is present in the ready-to-use antimicrobial formulations in quantities of 0.01% by weight to 5% by weight, based on the formulation as a whole. The ready-to-use formulations may be prepared from concentrates or solid mixtures containing about 3 to 50% by weight and preferably about 10 to 25% by weight of active substance.

What is claimed is:

1. The process of reducing the count of a virus comprising contacting said virus with (1) the reaction product of
       a) N-substituted propylenediamines corresponding to formula I:

$$R^1-NH-CH_2-CH_2-CH_2-NH_2 \qquad (I)$$

In which $R^1$ is a linear alkyl radical containing 12 to 14 carbon atoms, with
       b) compounds corresponding to formula II:

$$R^2-O-CO-CH_2-CH_2-\underset{\underset{NH_2}{|}}{CH}-COOH \qquad (II)$$

in which $R^2$ is an alkyl radical containing 1 to 4 carbon atoms or a hydrogen atom, the molar ratio of a) to b) is 1:1 to 1:2 and the reaction is carried out over a period of 0.5 to 10 hours at 60° C. to 175° C. with elimination of alcohol or water, and optionally, (2) wherein said reaction product is further reacted with ethylene oxide or propylene oxide, and optionally, (3) salt formation of the products obtained in (1) or (2) with inorganic or organic acids.

2. A process as in claim 1 wherein said virus is selected from lipophilic enveloped virus and lipophilic envelope-free virus.

* * * * *